(12) United States Patent
DeMayo

(10) Patent No.: US 9,314,272 B1
(45) Date of Patent: *Apr. 19, 2016

(54) MODULAR DISTRACTOR FOR USE IN ANKLE SURGERY

(75) Inventor: Edward DeMayo, Greenbrae, CA (US)

(73) Assignee: Innovative Medical Products, Inc., Plainville, CT (US)

( * ) Notice: Subject to any disclaimer, the term of this patent is extended or adjusted under 35 U.S.C. 154(b) by 381 days.

This patent is subject to a terminal disclaimer.

(21) Appl. No.: 13/134,238

(22) Filed: Jun. 3, 2011

(51) Int. Cl.
*A61B 17/60* (2006.01)
*A61B 17/66* (2006.01)
*A61B 17/02* (2006.01)
*A61B 17/68* (2006.01)

(52) U.S. Cl.
CPC .............. *A61B 17/66* (2013.01); *A61B 17/025* (2013.01); *A61B 17/60* (2013.01); *A61B 2017/681* (2013.01)

(58) Field of Classification Search
CPC ............ A61B 17/66; A61B 2017/681; A61B 17/025; A61B 2017/0268; A61B 2017/0275; A61B 17/60
USPC .............................. 606/90, 105; 600/227, 228
See application file for complete search history.

(56) References Cited

U.S. PATENT DOCUMENTS

| | | | | |
|---|---|---|---|---|
| 3,135,257 A * | 6/1964 | Anderson | ......................... | 602/39 |
| 3,976,061 A * | 8/1976 | Volkov et al. | .................... | 606/90 |
| 4,443,005 A * | 4/1984 | Sugarman et al. | ................ | 5/651 |
| 4,602,619 A * | 7/1986 | Wolf et al. | ..................... | 606/241 |
| 5,020,525 A * | 6/1991 | Ewing et al. | ..................... | 602/27 |
| 5,025,802 A * | 6/1991 | Laico et al. | .................... | 128/882 |
| 5,063,918 A * | 11/1991 | Guhl | ............................... | 602/40 |
| 5,213,094 A * | 5/1993 | Bonutti | ........................... | 601/33 |
| 5,290,220 A * | 3/1994 | Guhl | ............................. | 128/882 |
| 6,431,025 B1 * | 8/2002 | Koros et al. | ................ | 74/577 M |
| 7,003,827 B2 * | 2/2006 | DeMayo | ........................... | 5/600 |
| 7,380,299 B1 * | 6/2008 | DeMayo | ........................... | 5/648 |
| 7,665,167 B2 * | 2/2010 | Branch et al. | ..................... | 5/624 |
| 7,832,401 B2 * | 11/2010 | Torrie et al. | .................... | 128/845 |
| 2004/0015114 A1 * | 1/2004 | Hay | ................................ | 602/32 |
| 2008/0228191 A1 * | 9/2008 | Downs et al. | ................... | 606/90 |
| 2009/0105710 A1 * | 4/2009 | Saltzman et al. | ............... | 606/90 |
| 2011/0106094 A1 * | 5/2011 | Mitchell | ......................... | 606/90 |
| 2012/0205958 A1 * | 8/2012 | Colasanti et al. | ........ | 297/411.36 |

* cited by examiner

*Primary Examiner* — Anu Ramana
(74) *Attorney, Agent, or Firm* — Wasserbauer Law LLC; Damian Wasserbauer, Esq

(57) ABSTRACT

A manual distractor unit is mounted upon a support frame attached to an operating table side rail. A patient's knee support pad, extending from the distractor unit, is positioned under the patient's knee to provide traction to the patient's ankle, which is secured to the support frame.

2 Claims, 2 Drawing Sheets

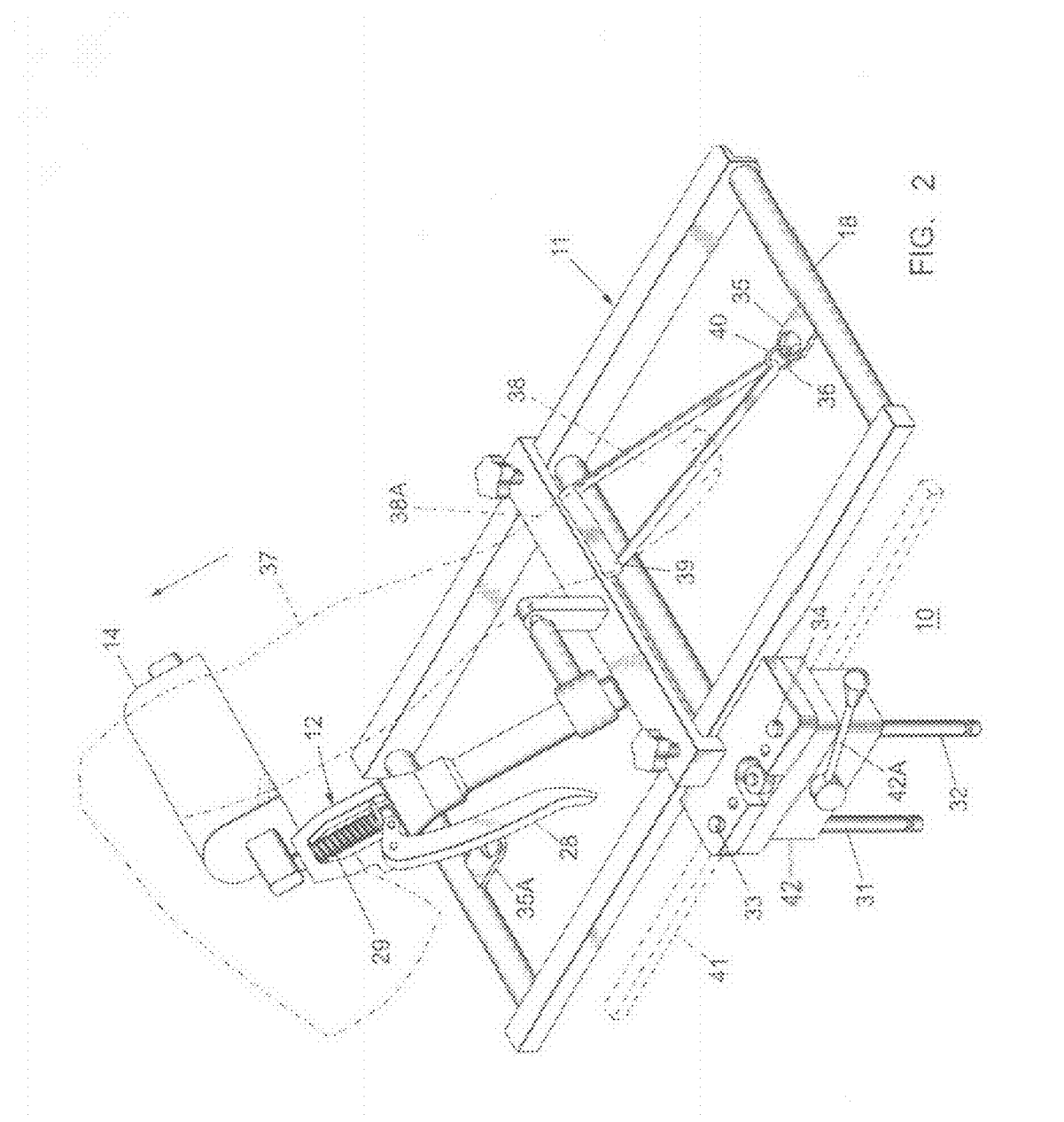

MODULAR DISTRACTOR FOR USE IN ANKLE SURGERY

BACKGROUND OF THE INVENTION

Methods currently available for ankle distraction procedures generally restrain the patient's leg and apply controlled pressure to the ankle for the required traction.

U.S. Pat. No. 5,290,220 entitled "Non-Invasive Distraction System for Ankle Arthroscopy" and U.S. Pat. No. 5,025,802 entitled "Surgical Holding Apparatus for Distracting Ankle" both describe applying such traction to the ankle directly.

The use of such equipment in the vicinity of the ankle could impair circumferential access to the patient's foot and ankle, during surgery, under some circumstances.

It has been shown that by restraining the patient's ankle with a simple strap and applying pressure to the underside of the patient's knee, the ankle can be distracted while allowing the surgeon complete access to the ankle in all directions.

On purpose of the instant invention is to provide a simple means of securing the patient's ankle while applying pressure to the underside of the patient's knee for such ankle arthroscopy by means of a manual distractor which can also be used for other joint athroscopic surgery.

SUMMARY OF THE INVENTION

One end of a manual distractor unit used in various joint distraction surgery is mounted to one end of a support frame attached to an operating table side rail. A patient's knee support pad, at an opposite end of the distractor unit, is positioned under the patient's knee to provide traction to the patient's ankle, which is secured by a strap to the support frame.

BRIEF DESCRIPTION OF THE DRAWINGS

FIG. 2 is a front perspective view of the patient's ankle distractor unit of FIG. 1 after attachment to the operating table with a portion of the patient's limb depicted in phantom thereon.

DESCRIPTION OF THE PREFERRED EMBODIMENT

Figure 1:
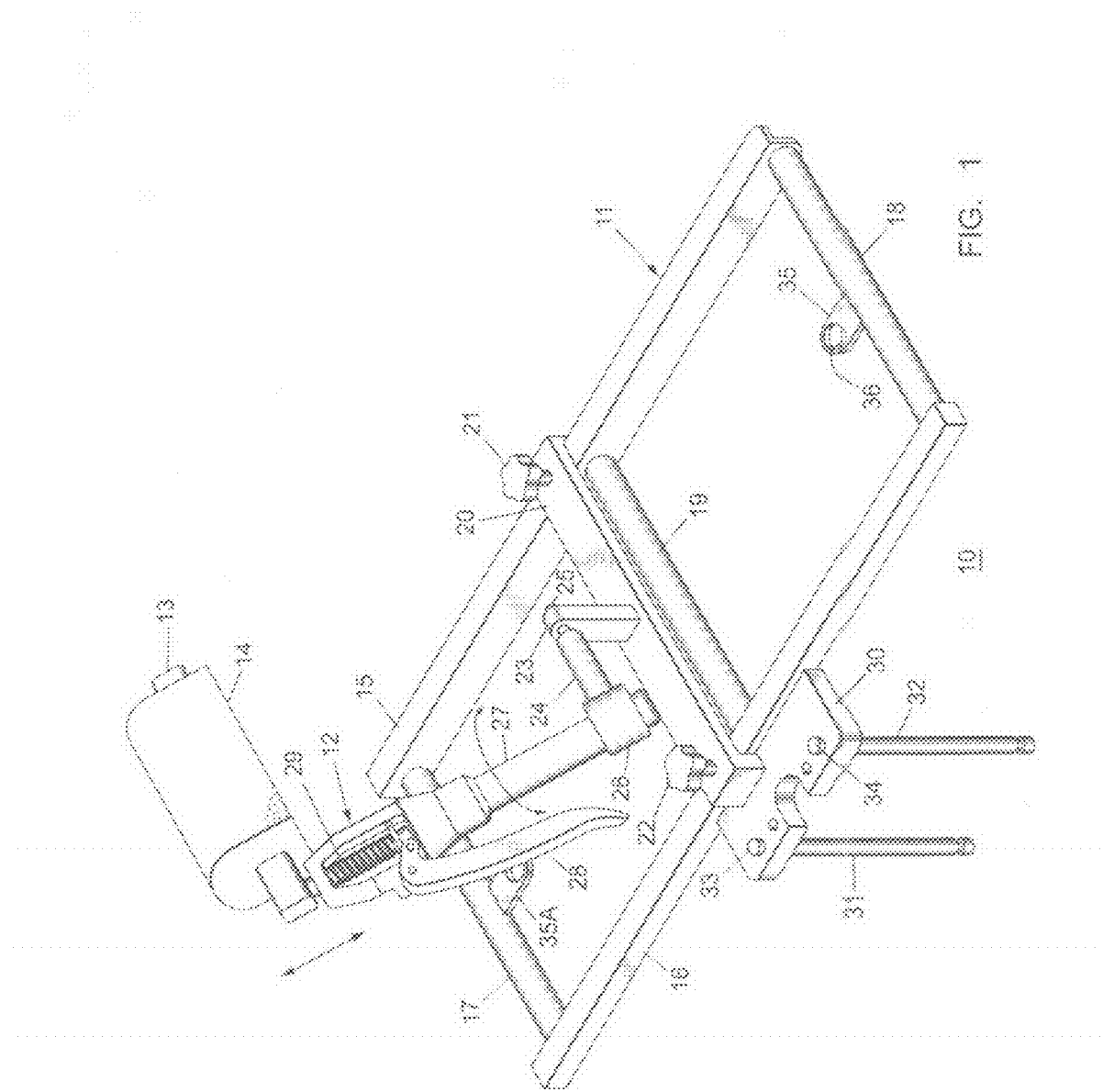
FIG. 1 is front perspective view of the modular patient's ankle distractor unit in accordance with the invention prior to attachment to the operating table.

As shown in FIG. 1, the modular ankle distractor unit 10 includes a support frame 11 and a manual distractor 12, which includes a support bar 13 for the patient support pad 14 for moving the support pad in the up and down directions, as indicated, in combination with the compression spring 29 and the distractor operating handle 28.

The manual distractor 12 is described within U.S. Pat. No. 8,048,082 entitled "Non-Invasive Femoral Distractor, which Application is incorporated herein for purposes of reference.

The support frame 11 includes a pair of side bars 15, 16, end bars 17, 18 and center bar 19.

A support bar 20 extends between the side bars 15, 16 and is attached thereto by means of threaded knobs 21 and 22. A post 23, upstanding from the support bar 20, is attached to a rod 24 by means of a bolt 25 and the rod 24 is welded to the support collar 26.

One end of the manual distractor cylinder 27 is arranged within the support collar 26 whereby the manual distractor 12 can be rotated in the clockwise and counter-clockwise directions, as indicated, by loosening the bolt 25.

The plate extension 30 on the end of the support bar 20 includes a pair of operating table connector posts 31, 32 attached thereto by means of bolts 33 and 34.

A tab 35 is attached to the end bar 18 and includes an opening 36 for receiving a clip connector 40 to retain the patient's foot strap 39, as shown in FIG. 2. A similar tab 35A is attached to the end bar 17.

Referring now to FIG. 2, the support frame 11 is depicted attached to an operating table side rail 41 by a side rail clamp 42 and operating handle 42A which engages the operating table connector posts 31, 32.

The side rail clamp 42 is similar to that described within U.S. Pat. No. 7,380,299 entitled "Operating Table Support Clamp".

To provide ankle distraction, a patient's limb 37 is arranged on the patient support pad 14 and the patient's foot 38 is secured within foot strap 39, which is secured to the end bar 18 by means of the tab 35, clip connector 40 and opening 36, as described earlier.

One such foot strap 39 is a Guhl Ankle Distractor Foot Strap obtained from Smith & Nephew Inc.

To provide distraction to the patient's ankle 38A, the distractor operating handle 28 on the manual distractor 12 is operated to move the patient support pad 14 and limb 37 in the indicated direction, while the ankle 38A is retained by virtue of the foot strap 39.

When the distraction of the ankle 38A is completed, the compression spring 29 allows the support pad 14 to return the limb 37 to the original position upon release of the distractor operating handle 28.

A simple and efficient arrangement has been described herein whereby a patient's ankle can be precisely distracted by use of a manual distractor that is used for other limb distraction as well.

What is claimed is:

1. A method for distracting a patient's ankle during surgery comprising the steps of:
    arranging a patient over a support frame on an operating table;
    positioning a knee of said patient over a U-shaped support pad disposed on one end of a manual distractor adapted to apply pressure to the popliteal area of a patient's knee when said manual distractor is extended linearly using an operating handle and a compression spring of said manual distractor;
    securing an ankle of said patient by a foot strap to an end bar of said support frame;
    compressing said manual distractor operating handle to extend said compression spring and move said patient's knee in a first direction away from said operating table to extend said patient's knee and distract said patient's ankle; and
    releasing said manual distractor operating handle to release said compression spring to move said patient's knee in a second direction, opposite said first direction and return said patient's knee to an original position after distraction of said patient's ankle.

2. A modular distractor unit for use in a procedure of an ankle distraction, comprising:
    a support frame comprising with a pair of first and second side bars connecting between a pair of first and second end bars, said support frame configured with means for connecting said support frame to a side rail of an operating table;

a manual distractor unit configured with a support bar at one end configured to extend said manual distractor linearly and an adjustable assembly at an opposite end configured to secure said manual distractor unit to said support frame and to provide rotatable adjustment of said manual distractor unit relative to said support frame, said support bar configured to receive a U-shaped support pad adapted to apply pressure to the popliteal area of a patient's knee when said manual distractor unit is extended linearly, said manual distractor unit further comprising a compression spring for moving said support bar in a first direction at the popliteal area to provide ankle distraction and for returning the patient's knee to an original position after the ankle distraction has been completed; and means for securing a patient's ankle to one of said pair of first and second end bars of said support frame during the ankle distraction.

\* \* \* \* \*